United States Patent [19]

Edwards et al.

[11] Patent Number: 4,787,406

[45] Date of Patent: Nov. 29, 1988

[54] FLUID FLOW CONTROL CLAMP AND METHOD FOR USING SAME

[75] Inventors: Fred Edwards, Orange; Eric Barr, Santa Ana, both of Calif.

[73] Assignee: Baxter International Inc., Deerfield, Ill.

[21] Appl. No.: 98,844

[22] Filed: Sep. 21, 1987

[51] Int. Cl.[4] .......................... F16L 55/14; F16K 7/06
[52] U.S. Cl. ........................................... 137/1; 251/8; 604/250
[58] Field of Search .................... 251/4, 6, 7, 8, 9, 205; 604/248, 250; 137/1

[56] References Cited

U.S. PATENT DOCUMENTS

| | | | |
|---|---|---|---|
| 715,429 | 12/1902 | Seabury | 251/8 |
| 2,215,725 | 9/1940 | Martinson | 27/23 |
| 2,314,767 | 3/1943 | Burrell | 251/122 |
| 2,908,476 | 10/1959 | Hidding | 251/8 |
| 3,167,085 | 1/1965 | Redmer | 251/8 |
| 3,332,439 | 7/1967 | Burke | 251/8 |
| 3,361,162 | 1/1968 | Prestridge et al. | 251/205 |
| 3,512,748 | 5/1970 | Wilson | 251/8 |
| 3,550,619 | 12/1970 | Halasz | 251/8 |
| 3,831,600 | 8/1974 | Yum et al. | 251/8 |
| 3,848,634 | 11/1974 | Noiles | 251/8 |
| 3,926,175 | 12/1975 | Allen et al. | 251/7 |
| 3,948,477 | 4/1976 | Lample | 251/8 |
| 3,993,076 | 11/1976 | Fogarty . | |
| 4,081,170 | 3/1978 | Doss, Jr. | 251/7 |
| 4,106,508 | 8/1978 | Berlin | 251/7 |
| 4,312,493 | 1/1982 | Stauffer | 251/8 |
| 4,337,791 | 7/1982 | Tech et al. | 251/8 |
| 4,475,709 | 10/1984 | Becker, Jr. | 251/6 |
| 4,482,347 | 11/1984 | Borsanyl | 604/153 |
| 4,575,041 | 3/1986 | Hu | 251/8 |

Primary Examiner—George L. Walton
Attorney, Agent, or Firm—Debra E. Dahl; Richard L. Myers; Gordon Peterson

[57] ABSTRACT

A clamp apparatus useful for controlling the flow of fluid through a flexible conduit which comprises: a resilient pad element adapted to aid in at least partially occluding the conduit; and a force system structured to be moved to at least partially occlude the flexible conduit such that when the force system is activated the flexible conduit contacts both the resilient pad element and the force system and the resilient pad element moves in response to the activation of the force system, provided that the force system is adapted to maintain the flexible conduit in at least one state of partial occlusion.

21 Claims, 1 Drawing Sheet

FLUID FLOW CONTROL CLAMP AND METHOD FOR USING SAME

BACKGROUND OF THE INVENTION

This invention relates to fluid flow control clamp systems and methods for controlling fluid flow. More particularly, the invention relates to such clamp systems and methods useful for controlling fluid flow rates in flexible conduits, e.g., tubing in intravenous systems.

Intravenous or IV systems are very important in caring for medical patients. Such systems are extensively used to provide one or more needed fluids, e.g., liquids, directly to the patient's vascular system. Of course, very careful control of the flow rate of any fluid passing into the patient's body is desirable. However, such control has been difficult to obtain.

Some of this difficulty results from the fact that the flexible conduit or tubing from the fluid source to the patient's body is small diameter. Also, the flow rates through such tubing are often relatively small. Flow control clamps currently in use are costly and/or structurally complicated and/or may not provide adequate control precision.

In preparing this application, the following U.S. Patents were considered: U.S. Pat. Nos. 2,215,725; 2,314,767; 3,948,477; 3,993,076; 4,106,508; 4,337,791; 4,475,709; and 4,482,347. Of these patents, both U.S. Pat. Nos. 3,993,076 and 4,106,508 disclose clamp devices for completely occluding blood vessels or other tubular conduits in animal bodies which involve resilient surfaces to reduce trauma caused by the complete occlusion. Devices disclosed in the other above-noted patents which relate to intravenous tubing do not include resilient surfaces since trauma caused to such tubing is of little or no concern.

Peristaltic pumps by necessity involve repeated opening and complete occlusion of a fluid containing conduit. In one particular such device, i.e., sold under the trademark AccuPro by Kendall McGaw of Irvine, Calif., rollers act to contact the periphery of the conduit with the conduit's periphery opposite the rollers contacting a resilient element. The action of each of these rollers causes the conduit to range from being open to being completely occluded, with no one degree or state of occlusion, e.g., partial occlusion, being maintained for any substantial period of time. Collectively, the rollers act on the conduit to provide the desired pumping action to the fluid in the conduit. With the rollers stopped, no fluid flows through the conduit.

SUMMARY OF THE INVENTION

A clamp apparatus and method useful for controlling the flow of fluid through a flexible conduit has been discovered. In one broad aspect, the invention involves a control clamp including a force means or system structured to be moved to at least partially occlude a flexible conduit. Further, when the force system is activated, the flexible conduit contacts both the force system and a resilient pad means or element which is adapted to aid in at least partially occluding the flexible conduit. This resilient pad element is structured to move in response to the activation of the force system. Moreover, the force system is adapted to maintain the flexible conduit, in which fluid is flowing, in at least one state of partial occlusion.

In another broad aspect, the present invention involves a method for controlling the flow rate of a fluid through a flexible conduit. This method comprises applying a substantially constant force to a first portion of the periphery of the conduit to partially occlude the conduit. A second portion of the conduit's periphery substantially opposite the first portion, is in contact with a resilient material which moved in response to the initial application of the force. In a further broad aspect, the flow rate of a fluid through a flexible conduit is adjusted by a method comprising adjusting the force (magnitude of force) applied to a first portion of the periphery of a flexible conduit, the force acting to partially occlude the conduit. During the adjusting, a second portion of the periphery of the flexible conduit substantially opposite the first portion is in contact with a resilient material which moves in response to the adjusting of the force.

The present invention provides substantial advantages. The clamp apparatus is relatively simple in structure, easy to operate and effective and reliable for its intended purpose. Importantly, the present apparatus has outstanding sensitivity which allows the fluid flow rate in the flexible conduit to be set precisely so that the apparatus can be used to meter fluid or as an off-on valve. Without limiting the invention to any theory of operation, it is believed that the movable, resilient pad or material causes the force system, in particular a force system having a substantially hemispherical portion which contacts the tubing, to have to travel a greater distance (relative to an unmoving, rigid pad or material) to obtain a given change in the degree of occlusion of the flexible conduit. This relatively greater distance provides a greater opportunity to precisely set the fluid flow rate in the conduit and, at least in part, provides the present invention with its outstanding control sensitivity.

The present clamp apparatus preferably further comprises a substantially rigid base adapted to carry the resilient pad element. A clamp housing is preferably included and adapted to hold the force system. In one embodiment, the substantially rigid base is a part, preferably an integral part, of the clamp housing. Also, it is preferred that the clamp housing include a passageway sized and adapted to allow the flexible conduit to pass therethrough. In a particularly useful embodiment, both the clamp housing and the force system include mutually mating threads which allow the force system to be moved with respect to the clamp housing, as desired. The clamp housing may be a molded or machined piece, e.g., of plastic The portion of the force system which contacts the flexible conduit is preferably substantially rigid. This portion may have any suitable configuration. Preferably, the portion of the force system useful for contacting the flexible conduit has a cross-sectional area at least equal to, and more preferably greater than, the normal inside diameter (with no occluding force being applied) (maximum inside dimension transverse to the direction of fluid flow) of the flexible conduit. Such sizing of this portion of the force system facilitates a wider range of degrees of partial occlusion and/or the complete occlusion, if necessary, of the flexible conduit. In one especially useful embodiment, the portion of the force system useful for contacting the flexible conduit has a substantially hemispherical configuration, preferably having a diameter larger than the normal inside diameter of the flexible conduit. This substantially hemispherical configuration advantageously provides for increased sensitivity, i.e., increased force system travel distance for each increment of change in degree of tubing occlusion.

The force system may be adapted to be activated manually, e.g., by a human moving the force system to a desired location, or automatically, e.g., by moving the force means using a motor or like device. For simplicity of construction and operation, in one embodiment it is preferred that the force system be structured to be manually activated.

In order to provide better control of the fluid flow rate through the flexible conduit, the force system is preferably adapted to maintain the flexible conduit in a plurality, more preferably a substantially continuous range, of different states of partial occlusion. The above-noted threaded force system is one particularly useful embodiment to achieve various states of partial occlusion of the flexible conduit.

The force system preferably moves toward and away from the resilient pad, more preferably in a direction substantially perpendicular to the longitudinal axis of the flexible conduit, in response to the force system being activated.

The movable, resilient pad element or material may be of any suitable configuration and made of any suitable material provided that it functions as described herein. In one embodiment the surface of the resilient pad element or material which contacts the flexible conduit is preferably normally substantially flat. By "normally" is meant when no force is being applied by the force system or the flexible conduit on the resilient pad element or material. Any one of numerous compositions may be used to make the resilient pad element or material. A particularly useful class of compositions are the elastomers, especially synthetic elastomer polymers. In any event such composition should have no substantial adverse effect on the flexible conduit, on the fluid in the conduit or on the other components of the present clamp apparatus. The resilient pad element is preferably secured, more preferably adhesively secured, to a substantially rigid base.

Although the present invention is particularly useful in controlling fluid flow in intravenous tubing, e.g., of conventional design and useful for conventional purposes, the present clamp and methods can be used to control fluid flow rates in various flexible, e.g., squeezable, conduits.

These and other aspects and advantages of the present invention are set forth in the following detailed description and claims, particularly when considered in conjunction with the accompanying drawings in which like parts bear like references numerals.

DETAILED DESCRIPTION OF EMBODIMENTS SHOWN IN DRAWING

Figure 1:
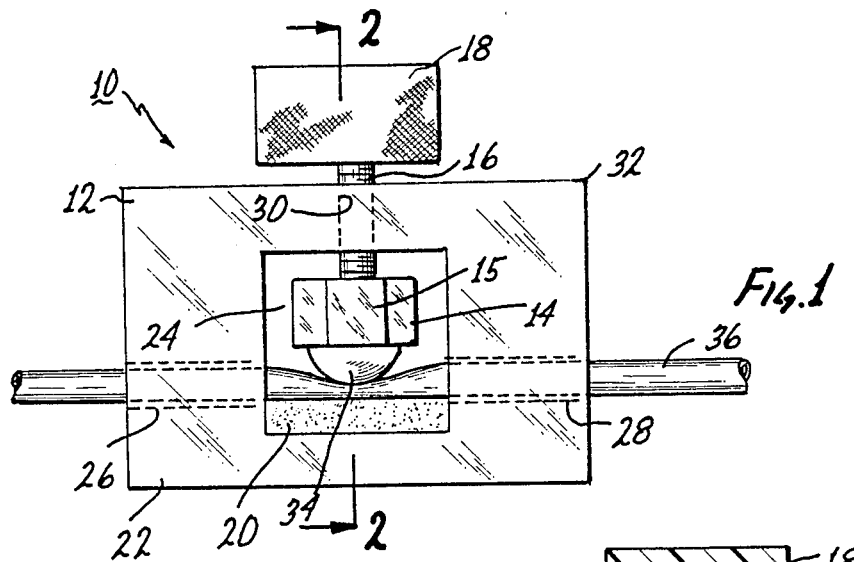
FIG. 1 is a front plan view showing an embodiment of the clamp apparatus of this invention.
Figure 2:
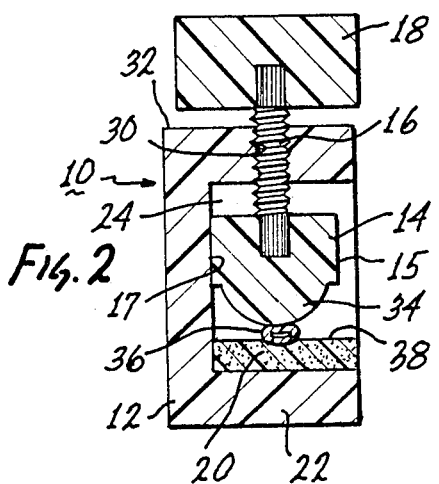
FIG. 2 is a cross-sectional view taken along line 2—2 of FIG. 1.

Referring now to the drawings, a flow control clamp according to the present invention, shown generally at 10, includes a rigid supporting structure or housing 12, a force-applying member in the form of a plunger 14, a threaded screw 16, a turn knob 18 and an elastomer pad 20. Housing 12 includes a base 22, a cavity 24, a first passage 26, a second passage 28 and a threaded hole 30 extending from cavity 24 to the top 32 of housing 12. Plunger 14 includes a depending, hemispherically-shaped force-applying surface or anvil 34.

Plunger 14 is situated in cavity 24 and has two, mutually opposing flat surfaces 15 and 17. Flat surface 17 buts up against housing 12 and thereby prevents turning of plunger 14. Threaded screw 16 extends into plunger 14 and is associated with plunger 14 such that when threaded screw 16 turns toward elastomer pad 20, plunger 14 moves toward elastomer pad 20. Elastomer pad 20, along with the fluid filled flexible intravenous tubing 36 acts to cause plunger 14 to move away from elastomer pad 20 when threaded screw 16 is turned away from elastomer pad 20. The threads of threaded screw 16 are sized and adapted to mate with the threads of threaded hole 30. Threaded screw 16 is also secured to turn knob 18 so that threaded screw 16 turns as turn knob 18 is turned.

Plunger 14 is substantially rigid and terminates at the end away from threaded screw 16 in the hemispherical-shaped anvil 34. The diameter of anvil 34 is larger than the diameter of the flexible intravenous tubing 36, the flow through which is to be controlled. In the embodiment shown in the drawings, the diameter of anvil 34 is approximately three (3) times the normal outside diameter of flexible intravenous tube or tubing 36 in the unstressed condition of the tubing 36. Plunger 14 and anvil 34 are situated and structured to apply a force to tubing 36 substantially perpendicular to the longitudinal axis of tubing 36 to squeeze tubing 36 between anvil 34 and elastomer pad 20 as plunger 14 moves down toward elastomer pad 20 in response to the turning of turn knob 18.

Tubing 36 is passed into housing 12 through first passage 26 and second passage 28, which are situated so that tubing 36 passes through cavity 24 between anvil 34 and elastomer pad 20.

Elastomer pad 20 is adhesively secured to base 22 and is located substantially within cavity 24. Elastomer pad 20 is situated and configured so as to present a normally substantially flat surface for contact with tubing 36. That is, the top surface 38 of elastomer pad 20 is substantially flat when anvil 34 is not in contact with tubing 36.

Figure 3:
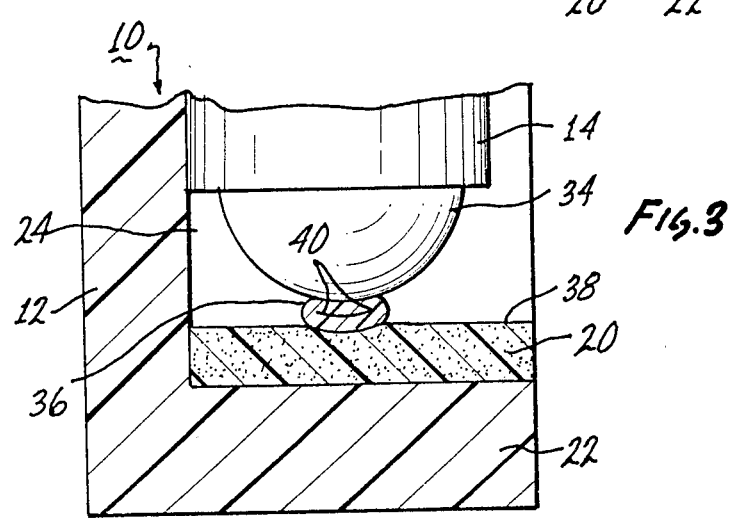
FIG. 3 is a detailed, side cross-sectional view of certain components of the embodiment shown in FIG. 1 demonstrating total occlusion of the intravenous tubing.

Elastomer pad 20 is constructed of resilient, synthetic elastomer polymer. The specific material used for elastomer pad 20 depends on the specific application involved and, in particular, on the material of construction and configuration of flexible tubing 36 and anvil 34. Elastomer pad 20 is preferably structured so that as anvil 34 contacts tubing 36 to further partially occlude tubing 36, a portion of the movement of anvil 34 is translated into movement, e.g., compression, of elastomer pad 20. Elastomer pad 20 preferably has sufficient rigidity so that it is possible to completely occlude tubing 36 using the movement of anvil 34, as desired, as indicated in FIG. 3.

The movement of elastomer pad 20 in response to the movement of anvil 34, as described above, results in anvil 34 having to transverse a greater distance to achieve a given change in the degree of occlusion of tubing 36 than would be the case if tubing 36 were placed on a rigid surface and then contacted with anvil 34. This greater distance, in turn, translates to more movement (turning) of turn knob 18 in order to achieve a given change in the degree of occlusion of tubing 36. The operator of turn knob 18 has more control over the degree of occlusion of tubing 36, e.g., can adjust the degree of occlusion by smaller increments. This increased occlusion control sensitivity is one important advantage of the present invention.

Although clamp 10 as shown is to be manually operated, such a device can be constructed to be automatically operated. A motor or similar device can be used to control the movement of plunger 14 and anvil 34.

Clamp 10 is structured so that once plunger 14 and anvil 34 are moved to achieve the desired degree of occlusion of tubing 36, that desired degree of occlusion is maintained until plunger 14 and anvil 34 are again manually moved. Thus, clamp 10 allows for a substantially continuous range of degrees of partial occlusion of tubing 36.

Clamp 10 functions as follows. Plunger 14 and anvil 34 are moved toward top 32 of housing 12 so that flexible tubing 36 can be passed into housing 12 through first passage 26 and second passage 28, Fluid, e.g., liquid, is caused to flow through tubing 36. Turn knob 18 is turned to cause anvil 34 to move into initial point contact with tubing 36. Turn knob 18 is further turned to move the anvil 34 farther downwardly to enlarge the point contact radially thereby flattening the tubing until the desired degree of partial occlusion of tubing 36, i.e., until the desired flow rate of fluid through tubing 36, is achieved. At this point, the turning is stopped and the desired fluid flow rate though tubing 36 is maintained. The force on tubing 36 can be adjusted, as desired, by moving anvil 34 up or down, as desired, to obtain a different degree of partial occlusion of tubing 36, i.e., a different fluid flow rate through tubing 36. If it is desired to completely stop the flow of fluid through tubing 36, turn knob 18 is turned until anvil 34 is moved so as to completely occlude tubing 36. The part spherical anvil 34 cooperates with the resilient pad 20 to effectively occlude the tubing 36 such that even the ends 40 (FIG. 3) of the passage through the tubing are completely closed. This state of total occlusion is maintained until turn knob 18 is manually turned to move anvil 34 away from elastomer pad 20.

The present system is mechanically simple, easy to operate and maintain, and provides effective and reliable control of fluid flow rates, e.g., of intravenous fluid flow rates. Importantly, the system provides for precise control of flow rates and for conveniently "fine tuning" such flow rates. In short, the apparatus and method of the present invention are both cost effective and operationally effective in controlling fluid flow rates.

While this invention has been described with respect to various specific examples and embodiments, it is to be understood that the invention is not limited thereto and that it can be variously practiced within the scope of the following claims.

What is claimed is:

1. A clamp apparatus for precisely controlling and metering the flow of fluid through a flexible conduit, comprising:
   (a) a resilient pad adapted to aid in partially occluding or completely occluding said conduit; and
   (b) a rigid force means structured to be moved to partially occlude a plurality of positions to maintain said flexible conduit in a plurality of different states of partial occlusion or in a state of complete occlusion, such that when said force means is activated or adjusted to various positions, said force means directly contacts said flexible conduit which in turn directly contacts and is supported by said resilient pad, and said resilient pad moves in response to said activation or adjustment of said force means, said resilient pad having sufficient rigidity to permit complete occlusion and sufficient resiliency to compress to varying degrees in response to movement of said force means towards said resilient pad, thereby permitting a continuous and wide range of small incremental adjustments in the degree of partial occlusion which in turn achieves a wide range of fluid flow rates.

2. The apparatus of claim 1 which further comprises substantially rigid base means adapted to carry said resilient pad means.

3. The apparatus of claim 2 wherein said resilient pad means is adhesively secured to said substantially rigid base means.

4. The apparatus of claim 1 wherein the portion of said force means which contacts said flexible conduit is substantially rigid.

5. The apparatus of claim 4 wherein said portion of said force means which contacts said flexible conduit is substantially hemispherical in configuration, said hemisphere having a larger diameter than the inside diameter of said flexible conduit.

6. The apparatus of claim 1 wherein said force means is structured to be manually activated.

7. The apparatus of claim 1 wherein said force means moves in a direction substantially perpendicular to the longitudinal axis of said conduit in response to said force means being activated.

8. The apparatus of claim 1 wherein the portion of said force means contacting said flexible conduit is substantially hemispherical in configuration.

9. The apparatus of claim 1 wherein the surface of said resilient pad means which contacts said conduit means is normally substantially flat.

10. The apparatus of claim 1 wherein said resilient pad means is constructed of elastomer material.

11. The apparatus of claim 1 which further comprises clamp housing means adapted to hold said force means.

12. The apparatus of claim 11 wherein said clamp housing means and said force means include mutually mating threads which allow said force means to be moved with respect to said clamp housing means.

13. The apparatus of claim 11 wherein said clamp housing means includes a substantially rigid base means adapted to carry said resilient pad means.

14. The apparatus of claim 13 wherein said clamp housing means includes a passageway sized and adapted to allow said flexible conduit to pass therethrough.

15. The apparatus of claim 11 wherein said clamp housing means includes a passageway sized and adapted to allow said flexible conduit to pass therethrough.

16. A method for precisely controlling and metering the flow rate of a fluid through a flexible conduit comprising the step of:
   (a) providing a rigid force means for applying and maintaining a substantially constant amount of force to a first portion of the periphery of said flexible conduit sufficient to partially occlude said flexible conduit to any one of a plurality of different states of partial occlusion or to completely occlude said flexible conduit, provided that a second portion of the periphery of said flexible conduit substantially opposite said first portion is in direct contact with and is supported by a resilient material which moves in response to the application of said force, said resilient material having sufficient rigidity to permit complete occlusion and sufficient resiliency to compress to varying degrees in response to application of varying amounts of said force against said flexible conduit, thereby permitting a continuous and wide range of small incremental adjustments in the degree of partial occlusion which in turn achieves a wide range of fluid flow rates.

17. The method of claim 16 wherein said force is applied in a direction substantially perpendicular to the longitudinal axis of said conduit.

18. The method of claim 16 wherein said force is applied manually.

19. A method according to claim 16, further comprising the steps of:
(b) adjusting and then maintaining the force applied in step (a), as desired, to change the degree of partial occlusion of said flexible conduit or to completely occlude said flexible conduit; and
(c) repeating step (b), as desired, to achieve varying degrees of partial occlusion or to completely occlude said flexible conduit.

20. A clamp for a flexible conduit comprising:
(a) a supporting structure;
(b) a resilient pad carried by the supporting structure and adapted to have the flexible conduit extend over the pad;
(c) a rigid force-applying member having an at least partially spherical force-applying surface; and
(d) means for mounting the force-applying member on the supporting structure for movement of the force-applying surface toward and away from the resilient pad whereby the flexible conduit can be squeezed between the resilient pad and the force-applying surface, said resilient pad having sufficient rigidity to permit complete occlusion and sufficient resiliency to compress to varying degrees in response to application of the force-applying surface against said flexible conduit, thereby permitting a continuous and wide range of small incremental adjustments in the degree of partial occlusion which in turn achieves a wide range of fluid flow rates.

21. The clamp of claim 20 whereas the mounting means mounts the force-applying member for linear movement toward and away from the resilient pad.

* * * * *

UNITED STATES PATENT AND TRADEMARK OFFICE
CERTIFICATE OF CORRECTION

PATENT NO. : 4,787,406

DATED : November 29, 1988

INVENTOR(S) : Fred Edwards and Eric Barr

It is certified that error appears in the above-identified patent and that said Letters Patent is hereby corrected as shown below:

IN THE CLIAMS:

Claim 1, column 5, line 64, delete "partially occlude".

Signed and Sealed this

Eighth Day of August, 1989

Attest:

DONALD J. QUIGG

Attesting Officer

Commissioner of Patents and Trademarks